(12) United States Patent
Lee et al.

(10) Patent No.: US 10,959,730 B2
(45) Date of Patent: Mar. 30, 2021

(54) CLIPPING DEVICE FOR ENDOSCOPE

(71) Applicant: AJOU UNIVERSITY INDUSTRY-ACADEMIC COOPERATION FOUNDATION, Suwon-si (KR)

(72) Inventors: Moon Gu Lee, Gwacheon-si (KR); Yong Ho Jeon, Suwon-si (KR); Byung Kyu Kim, Gimpo-si (KR); Chang Ho Jung, Seoul (KR); Chan Joong Kim, Taean-gun (KR)

(73) Assignee: AJOU UNIVERSITY INDUSTRY-ACADEMIC COOPERATION FOUNDATION, Suwon-si (KR)

( * ) Notice: Subject to any disclaimer, the term of this patent is extended or adjusted under 35 U.S.C. 154(b) by 113 days.

(21) Appl. No.: 16/185,630

(22) Filed: Nov. 9, 2018

(65) Prior Publication Data

US 2019/0142426 A1 May 16, 2019

(30) Foreign Application Priority Data

Nov. 10, 2017 (KR) .......................... 10-2017-0149850

(51) Int. Cl.
  *A61B 17/10* (2006.01)
  *A61B 17/08* (2006.01)

(52) U.S. Cl.
  CPC ............ *A61B 17/10* (2013.01); *A61B 17/083* (2013.01)

(58) Field of Classification Search
  CPC ....... A61B 17/08; A61B 17/083; A61B 17/10; A61B 17/122; A61B 17/1227; A61B 17/128; A61B 17/1285; A61B 2017/00004; A61B 2017/00296; A61B 2017/00876; A61B 2017/081
  See application file for complete search history.

(56) References Cited

U.S. PATENT DOCUMENTS

| | | | |
|---|---|---|---|
| 7,691,104 B2 | 4/2010 | Yamamoto et al. | |
| 2006/0224165 A1* | 10/2006 | Surti | A61B 17/29 606/142 |
| 2007/0112359 A1* | 5/2007 | Kimura | A61B 17/1222 606/142 |

(Continued)

FOREIGN PATENT DOCUMENTS

| JP | 4373715 B2 | 11/2009 |
|---|---|---|
| KR | 10-2014-0049724 A | 4/2014 |
| KR | 10-2017-0041620 A | 4/2017 |

*Primary Examiner* — Melanie R Tyson
(74) *Attorney, Agent, or Firm* — Sughrue Mion, PLLC (57) ABSTRACT

The clipping device includes a connecting portion which is moved while being connected to a wire of the endoscope and has a body broken when tension more than a set value is applied thereto, a body portion which includes a first inside path portion through which the connecting portion moves and has a magnetic force, a cap portion which is located on a side of the body portion, includes a second inside path portion connected to the first inside path portion, and guides movement of the connecting portion, a clipping portion which is connected to the connecting portion protruding through the cap portion and contracts due to movement of the connecting portion to grip body tissue, and a connector which connects the body portion to the cap portion and includes a material biodegradable in a human body.

6 Claims, 13 Drawing Sheets

(56) References Cited

U.S. PATENT DOCUMENTS

2007/0135678 A1\* 6/2007 Suzuki .............. A61B 17/1285
600/37
2015/0142025 A1\* 5/2015 Brandeis .................. A61F 2/01
606/151

\* cited by examiner

CLIPPING DEVICE FOR ENDOSCOPE

CROSS-REFERENCE TO RELATED APPLICATION

This application claims priority to and the benefit of Korean Patent Application No. 2017-0149850, filed on Nov. 10, 2017, the disclosure of which is incorporated herein by reference in its entirety.

BACKGROUND

1. Field of the Invention

The present invention relates to a clipping device for an endoscope, and more particularly, to a clipping device for an endoscope capable of easily separating a part of gripped body tissue of a patient from a body having a magnetic force.

2. Discussion of Related Art

Generally, an endoscope is a medical machine which observes an inside of a human body. Endoscopes are classified into a bronchoscope, a gastroscope, a laparoscope, and an anoscope depending on a part to be inspected and a method of observing an object to be observed.

Endoscopes include a direct scope, which has one tube and allows internal organs to be directly seen with the naked eye, a type using a lens system, a type which directly inserts a camera into internal organs, and a fiber scope using glass fibers, and the like. During an endoscopic surgery, perforations may occur and a part which needs suturing is sutured using an endoscopic clip or a surgical suture.

During a conventional process of separating a magnetic body connected to a clip which grips body tissue of a patient, an affected area may be irritated. Accordingly, it is necessary to make improvements thereto.

As a related art of the present invention, Korean Patent Publication No. 2014-0049724 (published on Apr. 28, 2014) discloses a medical surgical instrument.

SUMMARY OF THE INVENTION

The present invention is directed to providing a clipping device for an endoscope capable of easily separating a part of gripped body tissue of a patient from a body having a magnetic force.

According to an aspect of the present invention, there is provided a clipping device for an endoscope. The clipping device includes a connecting portion which is moved while being connected to a wire of the endoscope and has a body thereof broken when tension more than a set value is applied thereto, a body portion which includes a first inside path portion through which the connecting portion moves and which has a magnetic force, a cap portion which is located on a side of the body portion, includes a second inside path portion connected to the first inside path portion, and guides movement of the connecting portion, a clipping portion which is connected to the connecting portion protruding through the cap portion and contracts due to movement of the connecting portion to grip body tissue, and a connector which connects the body portion to the cap portion and includes a material biodegradable in a human body.

The connecting portion may include a first body connected to the wire, a second body connected to the clipping portion, and a breaking body which connects the first body to the second body and is broken when tension more than a set value is applied thereto.

The body portion may have a pipe shape, and both longitudinal sides of the body portion may have magnetic forces of different polarities.

The body portion may include a combination groove formed on an outside thereof to be combined with at least one of the cap portion and the connector.

The cap portion may include a first cap body in contact with an end of the body portion, a second cap body installed while being spaced apart from the first cap body, and a connecting body which connects the first cap body to the second cap body and includes an outer diameter smaller than an outer diameter of the first cap body. Here, the second inside path portion may be formed inside the first cap body, the connecting body, and the second cap body.

The connector may be installed in a shape which surrounds an outside of the connecting body and an outside of the body portion facing the connector.

The cap portion may include a first support body in contact with an end of the body portion, a second support body connected to the first support body with a step therebetween, and a cap connecting portion which extends from the second support body, is held by an outside the body portion, and is broken by a set external force. Also, the second inside path portion may be formed inside the first support body and the second support body.

The connector may be installed in a shape which surrounds an outside of the first support body and an outside of the body portion facing the first support body.

The connector may include gelatin.

BRIEF DESCRIPTION OF THE DRAWINGS

The above and other objects, features and advantages of the present invention will become more apparent to those of ordinary skill in the art by describing exemplary embodiments thereof in detail with reference to the accompanying drawings, in which.

DETAILED DESCRIPTION OF EXEMPLARY EMBODIMENTS

Hereinafter, a clipping device for an endoscope according to one embodiment of the present invention will be described with reference to the attached drawings. In this process, a thickness of lines, a size of a component, or the like shown in the drawings may be exaggerated for clarity and convenience of description.

Also, the following terms are defined in consideration of functions thereof in the present invention and may vary according to the intention of a user or an operator or practice. Accordingly, definitions of the terms will be determined on the basis of the content throughout the specification.

Figure 1:
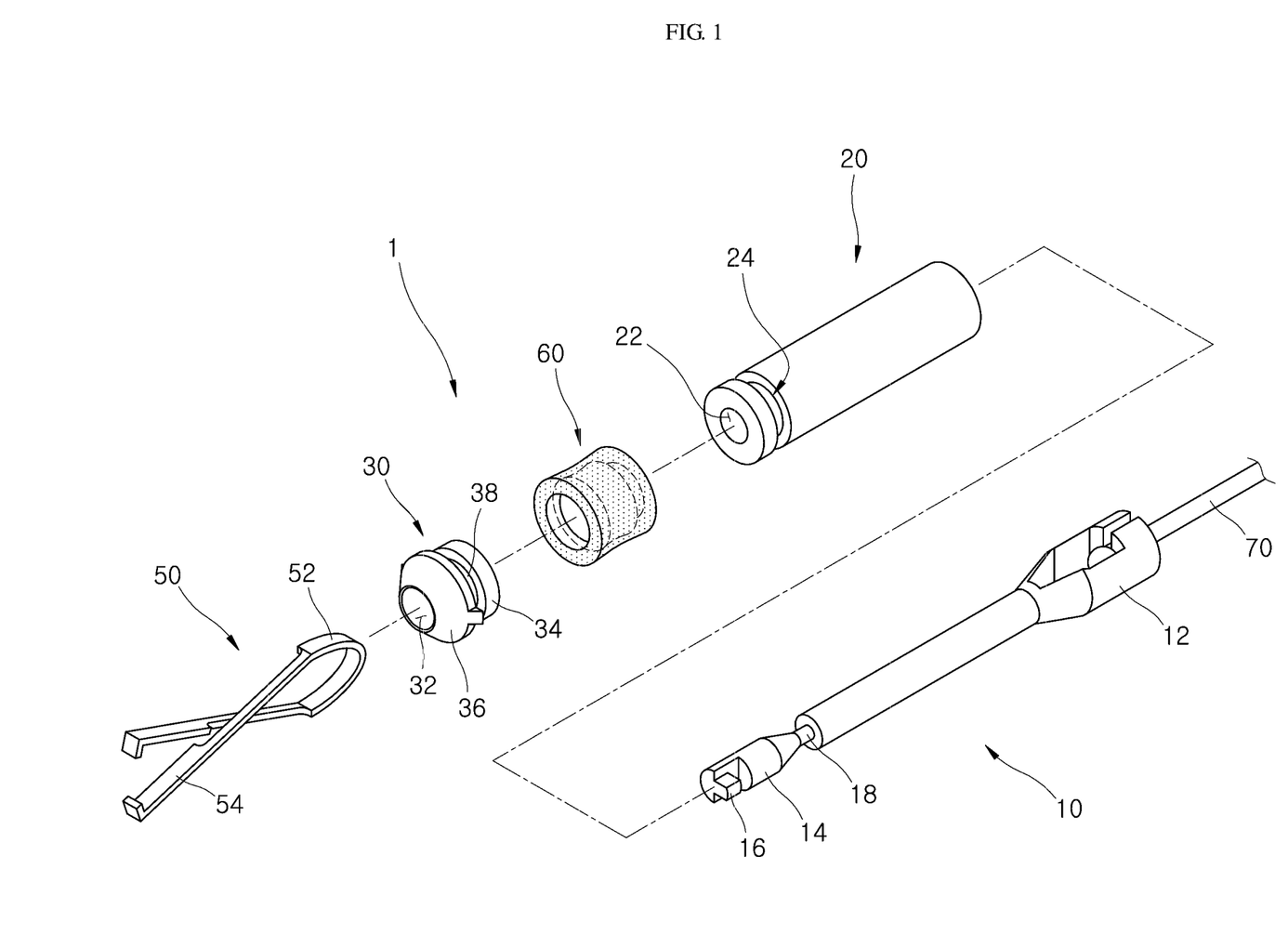
FIG. 1 is an exploded perspective view of a clipping device for an endoscope according to one embodiment of the present invention.
Figure 2:
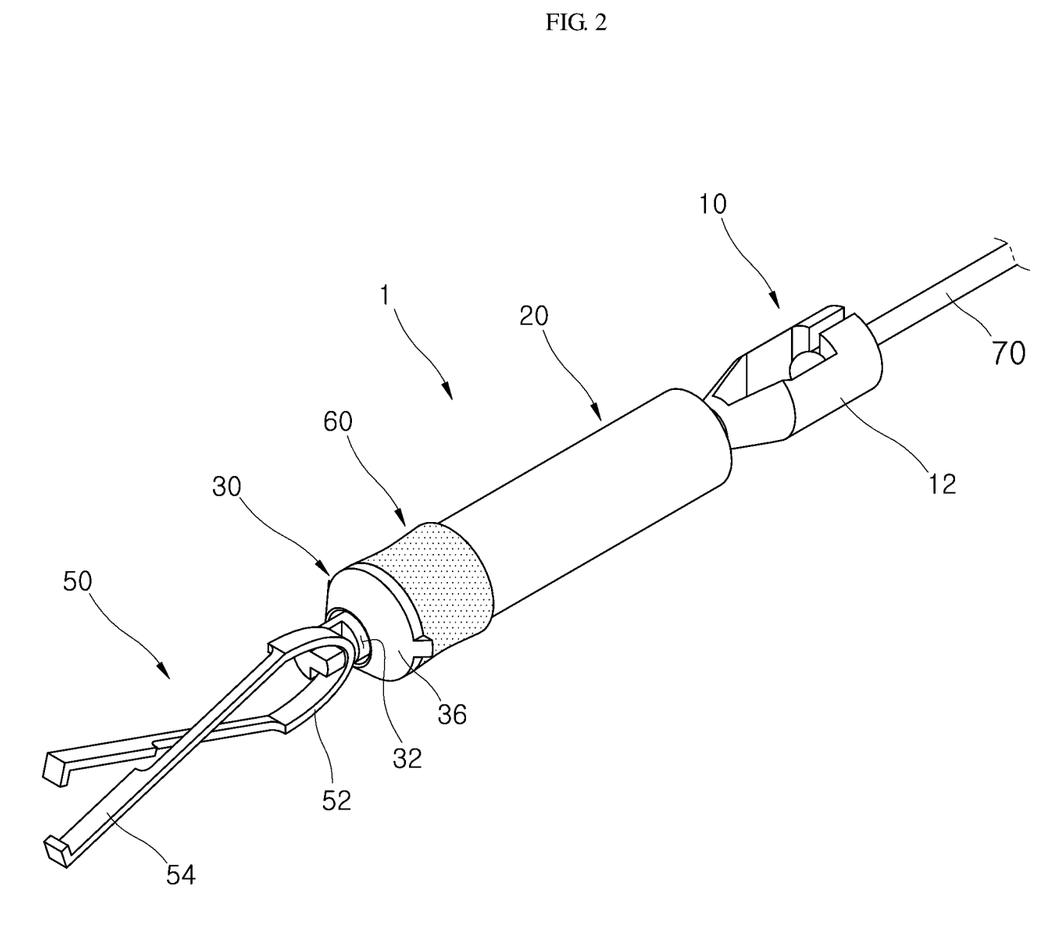
FIG. 2 is a perspective view of the clipping device for an endoscope according to one embodiment of the present invention.
Figure 3:
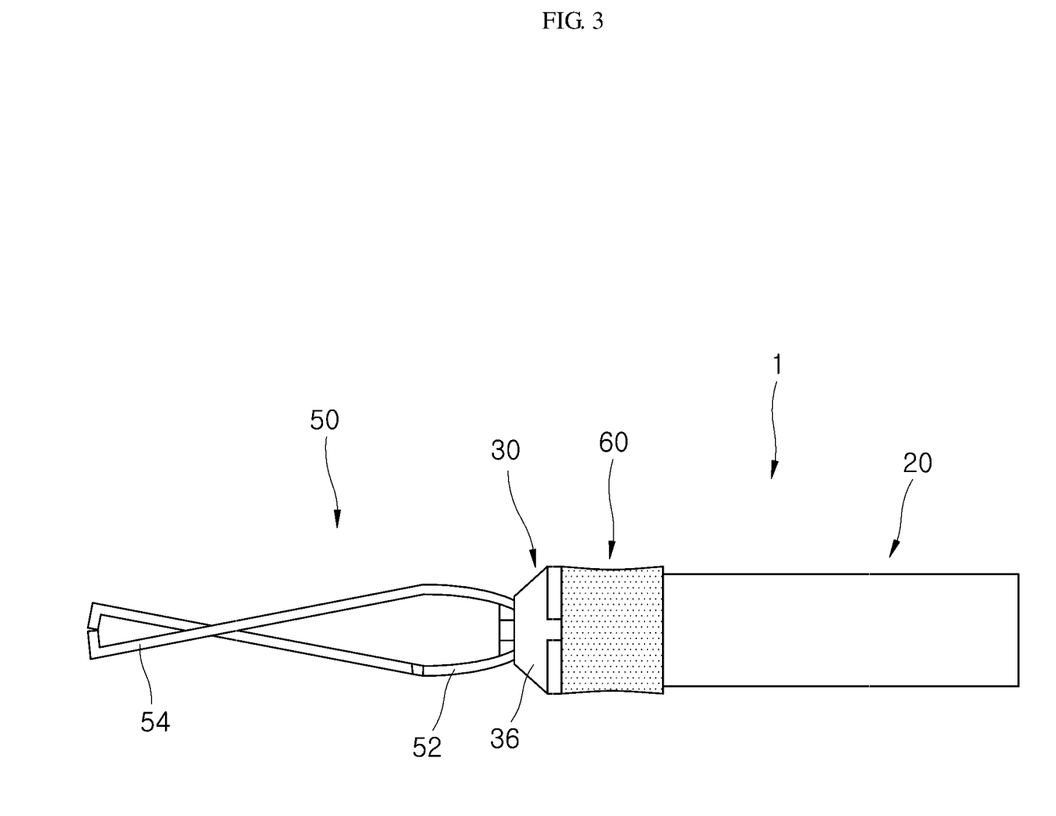
FIG. 3 is a view illustrating a state in which a first body is separated from the clipping device for an endoscope according to one embodiment of the present invention.
Figure 4:
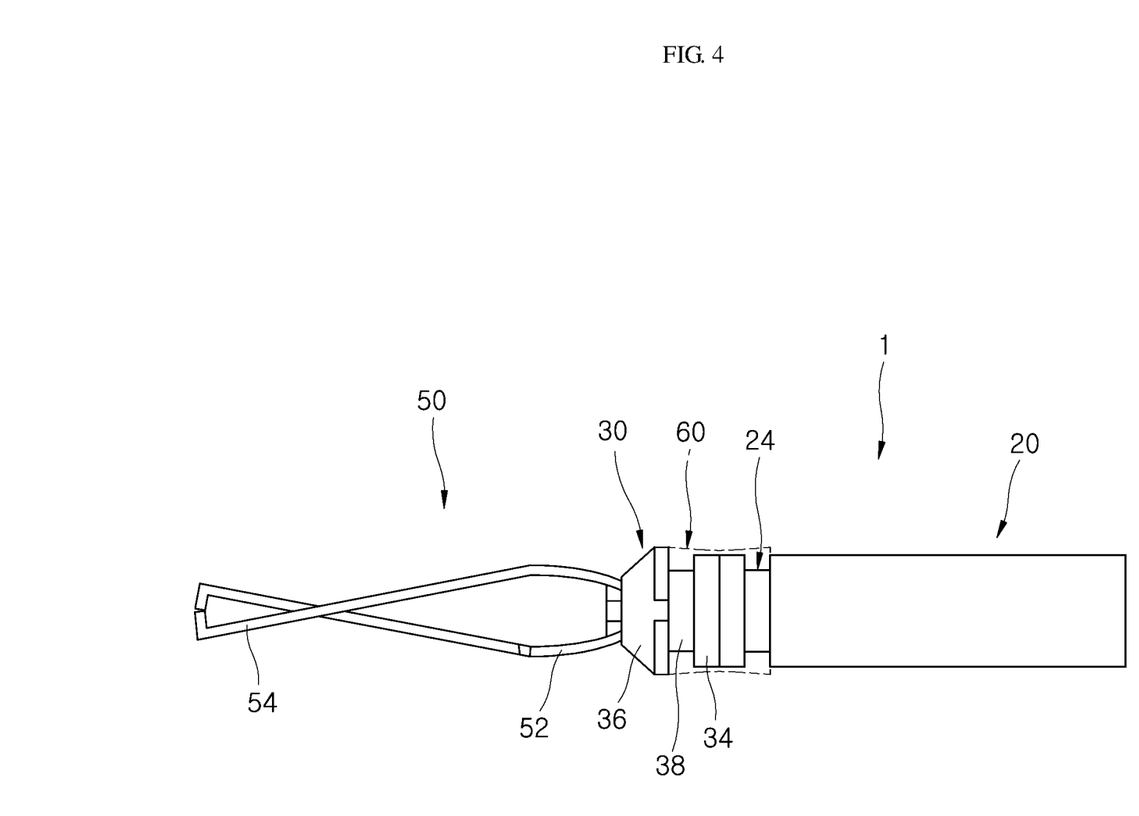
FIG. 4 is a view illustrating a state in which a connector has been biodegraded according to one embodiment of the present invention.
Figure 5:
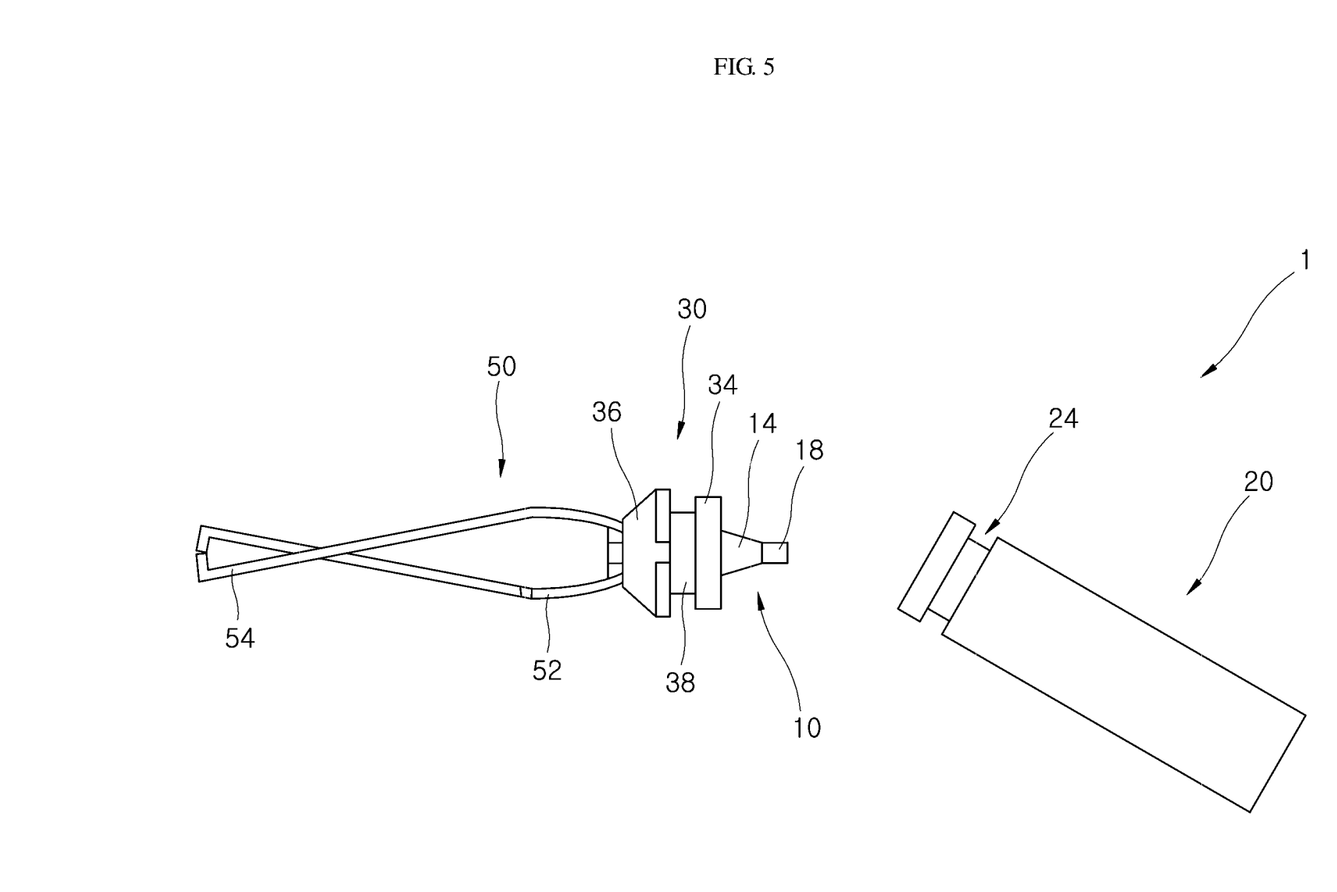
FIG. 5 is a view illustrating a state in which a body portion is separated from a cap portion according to one embodiment of the present invention.

FIG. 1 is an exploded perspective view of a clipping device for an endoscope according to one embodiment of the present invention. FIG. 2 is a perspective view of the clipping device for an endoscope according to one embodiment of the present invention. FIG. 3 is a view illustrating a state in which a first body is separated from the clipping device for an endoscope according to one embodiment of the present invention. FIG. 4 is a view illustrating a state in which a connector has been biodegraded according to one embodiment of the present invention. FIG. 5 is a view illustrating a state in which a body portion is separated from a cap portion according to one embodiment of the present invention.

An endoscope is a useful medical apparatus capable of viewing a state of an inside of an organ such as a stomach, a large intestine, and the like. Due to the nature of an endoscope entering through a mouth or an anus, an incision is not performed outside a body and a variety of treatments such as an inspection, a diagnosis, sampling, a suture, and the like may be performed using specialized tools with a camera for observation. Also, since it is possible to directly access internal organs without an external incision by using an endoscope, recovery after treatment is fast. However, due to the nature of an endoscope device, it is necessary to manufacture a small and thin tool for treatment less than a certain diameter.

Also, a clipping portion 50 shown in FIG. 1 is used for performing a suturing operation using an endoscope. Suturing is performed by holding both ends of tissue by using the metallic clipping portion 50 and pulling and sticking them together with a strong force.

As shown in FIGS. 1 to 3, a clipping device 1 according to one embodiment of the present invention includes a connecting portion 10, which moves while being connected to a wire 70 of an endoscope and of which a body is broken when tension at or above a set value is applied, a body portion 20, which includes a first inside path portion 22 through which the connecting portion 10 moves and which has a magnetic force, a cap portion 30, which is located on a side of the body portion 20 and includes a second inside path portion 32 connected to the first inside path portion 22 so as to guide movement of the connecting portion 10, the clipping portion 50, which is connected to the connecting portion 10 protruding through the cap portion 30 and grips body tissue while contracting due to movement of the connecting portion 10, and a connector 60 which connects the body portion 20 and the cap portion 30 to each other and is formed of a material biodegradable in a human body.

As shown in FIGS. 1 and 2, the clipping portion 50 in front of the body portion 20 (a left side based on FIG. 1) is connected to the connecting portion 10 and operates in a contracted shape while the connecting portion 10 is moved by movement of the wire 70 at a suture position during endoscopy.

As shown in FIGS. 1 and 3, when the connecting portion 10 is pulled, the metallic clipping portion 50 held by a connecting hook 16 of the connecting portion 10 is folded and enters an inside of the cap portion 30. When tension higher than a set value is transferred to a breaking body 18, a thin middle part of the breaking body 18 is broken by the tension and a second body 14 connected to the clipping portion 50 remains inside the cap portion 30 and a first body 12 is separated toward an outside of the body portion 20.

The connecting portion 10 may have a variety of shapes which fall within the technical concept of moving while being connected to the wire 70 of the endoscope and in which a body thereof is broken when tension higher than a set value is applied thereto. The connecting portion 10 according to one embodiment includes the first body 12, the second body 14, the connecting hook 16, and the breaking body 18.

Since the first body 12 is connected to the wire 70, the first body 12 moves when the wire 70 moves. One side of the first body 12 according to one embodiment is located outside the body portion 20, and the other extends through the first inside path portion 22 of the body portion 20. An outer diameter of the first body 12 is greater than an inner diameter of the body portion 20 such that the first body 12 does not move toward the inside of the body portion 20 and remains in a state of being held on an outside of the body portion 20.

The second body 14 may have a variety of shapes which fall within the technical concept of being connected to the clipping portion 50 and being moved inside or outside the cap portion 30 along with the clipping portion 50. The second body 14 includes the connecting hook 16 combined with a gripped hook portion 52 of the clipping portion 50. Since the connecting hook 16 protrudes from the second body 14 and the gripped hook portion 52 of the clipping portion 50 is held by the connecting hook 16, the second body 14 and the clipping portion 50 move together.

The breaking body 18 may have a variety of shapes which fall within the technical concept of connecting the first body 12 and the second body 14 to each other and being broken when tension higher than a set value is applied thereto. The second body 14 is connected to one side of the breaking body 18 (a left side based on FIG. 1), and the first body 12 is connected to the other side of the breaking body 18 (a right side based on FIG. 1). Since outer diameters of the second body 14 and the breaking body 18 are smaller than an inner diameter of the second inside path portion 32, the second body 14 and the breaking body 18 move along an internal space of the cap portion 30. Since the breaking body 18 includes a part with an outer diameter thereof gradually decreased, when tension occurs in a laterally horizontal direction (based on FIG. 1), a smallest vertical cross section of the breaking body 18 is broken at tension higher than the set value. Accordingly, the first body 12 and the wire 70 move together, and the connecting portion 10 except for the first body 12 is located inside the cap portion 30 and the body portion 20.

The body portion 20, which is magnetic, may have a variety of shapes which fall within the technical concept of including the first inside path portion 22 through which the connecting portion 10 moves. The body portion 20 according to one embodiment has a pipe shape, and both longitudinal sides of the body portion 20 have magnetic forces having different polarities. Also, the body portion 20 includes a combination groove 24 for being combined with at least one of the cap portion 30 and the connector 60 is formed along an outer perimeter of the body portion 20, which faces the cap portion 30, in a circumferential direction. Accordingly, when the clipping devices 1 for an endoscope are consecutively installed, the body portions 20 having magnetic forces come into contact with one another, and thus treatment of suturing perforation of an affected area may be performed easily by moving body tissue gripped by the clipping portion 50.

The connecting portion 10 sequentially passes through the body portion 20 and the inside of the cap portion 30 and is connected to the clipping portion 50. In the body portion 20, a permanent magnet is used and an electromagnet may be used as necessary.

The body portion 20 includes the first inside path portion 22, through which the connecting portion 10 moves, and is connected to the cap portion 30 continuously. The body portion 20 and the cap portion 30 are connected by the connector 60, and the connecting portion 10 is horizontally moved along the first inside path portion 22 formed inside the body portion 20.

The clipping portion 50 may have a variety of shapes which fall within the technical concept of being located opposite to the wire 70 on the basis of the body portion 20, being connected to the connecting portion 10 protruding through the cap portion 30, and contracting due to movement of the connecting portion 10 to grip body tissue. The clipping portion 50 according to one embodiment includes the gripped hook portion 52 and a grip portion 54.

The gripped hook portion 52 has a hook shape which is held by the connecting hook 16 of the connecting portion 10. The grip portion 54 extends from the gripped hook portion 52 and opens in a tweezers shape and is held by the cap portion 30 due to movement of the connecting portion 10 such that two separate ends may be collected so as to grip body tissue.

The cap portion 30 may have a variety of shapes which fall within the technical concept of being located on the side of the body portion 20 and including the second inside path portion 32 connected to the first inside path portion 22 to guide movement of the connecting portion 10. The cap portion 30 according to one embodiment includes the second inside path portion 32, a first cap body 34, a second cap body 36, and a connecting body 38.

The first cap body 34 has a pipe shape in contact with an end of the body portion 20 and has a similar outer diameter to that of the body portion 20. The second body 14 is installed while being spaced apart from the first cap body 34 and has a conical shape. The connecting body 38 connects the first cap body 34 and the second cap body 36 to each other and includes an outer diameter smaller than an outer diameter of the first cap body 34 so as to form a groove portion for allowing the connector 60 to be inserted therein and held thereby.

Since the second inside path portion 32 is formed inside the first cap body 34, the connecting body 38, and the second cap body 36, the connecting portion 10 may move inside the first cap body 34, the connecting body 38, and the second cap body 36 through the second inside path portion 32. The connecting hook 16 of the connecting portion 10 connected to the wire 70 protrudes outward from the cap portion 30 and is connected to the gripped hook portion 52 of the clipping portion 50. When tension higher than a set value is transferred to the connecting portion 10, the first body 12 and the second body 14 are separated from each other on the basis of the breaking body 18 and the second body 14 connected to the clipping device 50 is located inside the cap portion 30.

The connector 60 may be variously modified within the technical concept of connecting the body portion 20 and the cap portion 30 to each other and being formed of a material which is biodegradable in a human body. The connector 60 according to one embodiment is installed to surround an outside of the connecting body 38 and the outside of the body portion 20 which faces the connector 60. Also, the connector 60 includes gelatin to be biodegraded in a human body such that the cap portion 30 and the body portion 20 may be easily separated from each other.

When perforation is completely sutured through an operation of the clipping portion 50, the connector 60, which is the connecting portion 10 between the cap portion 30 and the body portion 20, which is magnetic, is gradually melted and removed such that the clipping portion 50 and the cap portion 30 are separated from the body portion 20, which is magnetic.

The connector 60 includes a biodegradable material with gelatin as a main material and may additionally include at least one of any material which is biodegraded in the digestive system. The connector 60 according to one embodiment has a pipe shape. One side of the connector 60 forms a protrusion, which is inserted into and held by the combination groove 24 of the body portion 20, and the other forms a protrusion, which is inserted into a groove portion formed outside the connecting body 38 of the cap portion 30. A combination force between the cap portion 30 and the body portion 20 is improved by installing the connector 60.

Hereinafter, an operation state of the clipping device 1 according to one embodiment of the present invention will be described in detail with reference to the attached drawings.

As shown in FIGS. 1 and 2, while the body portion 20 and the cap portion 30 are in contact with each other, the connector 60 is inserted into the combination groove 24 formed outside the body portion 20 and a groove portion outside the connecting body 38 formed outside the cap portion 30 so as to connect the cap portion 30 to the body portion 20. Here, the connector 60 is molded including gelatin, which is biodegradable in the intestines.

When the clipping device 1 for an endoscope is located inside a human body and the grip portion 54 of the clipping portion 50 contracts due to the movement of the connecting portion 10 as shown in FIG. 3, the connector 60 formed of gelatin is gradually biodegraded and discharged as shown in FIG. 4.

As shown in FIG. 5, as time passes, the connector 60 formed of gelatin is gradually removed, and the body portion 20 is separated from the cap portion 30. After the body portion 20, which is magnetic, is separated from the cap portion 30 connected to the clipping portion 50, the body portion 20, which is magnetic, is taken out from the body by using suction which is used when the clipping portion 50 is pulled therefrom.

Meanwhile, according to one embodiment of the present invention, gelatin may be used for the connector 60, but the connector 60 may be molded using a different biodegradable material.

Hereinafter, a clipping device 5 for an endoscope according to another embodiment of the present invention will be described with reference to the drawings.

For convenience of description, elements having the same configuration and performing the same operation as those of one embodiment of the present invention will be referred to as the same reference numerals and a detailed description thereof will be omitted.

Figure 6:
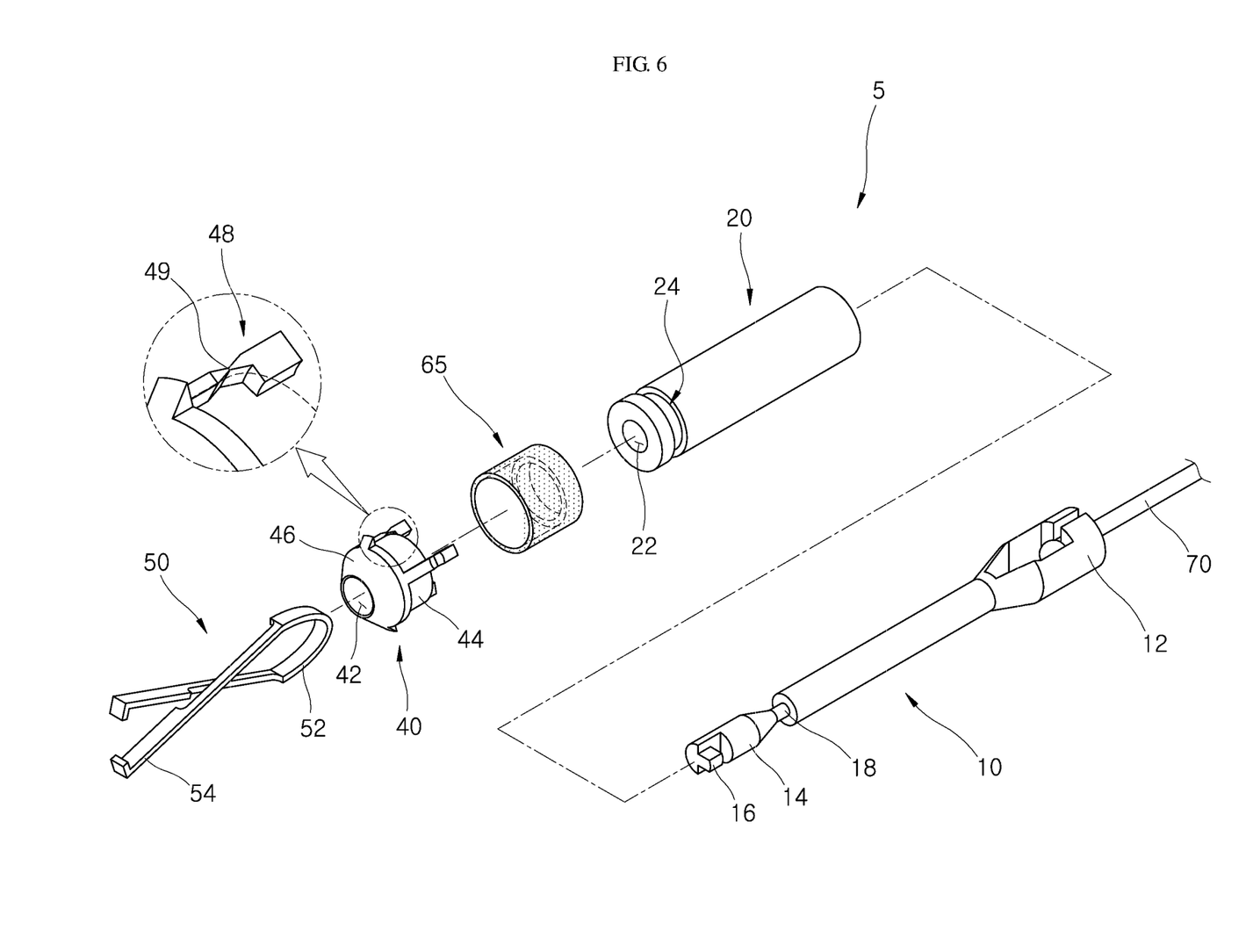
FIG. 6 is an exploded perspective view of a clipping device for an endoscope according to another embodiment of the present invention.
Figure 7:
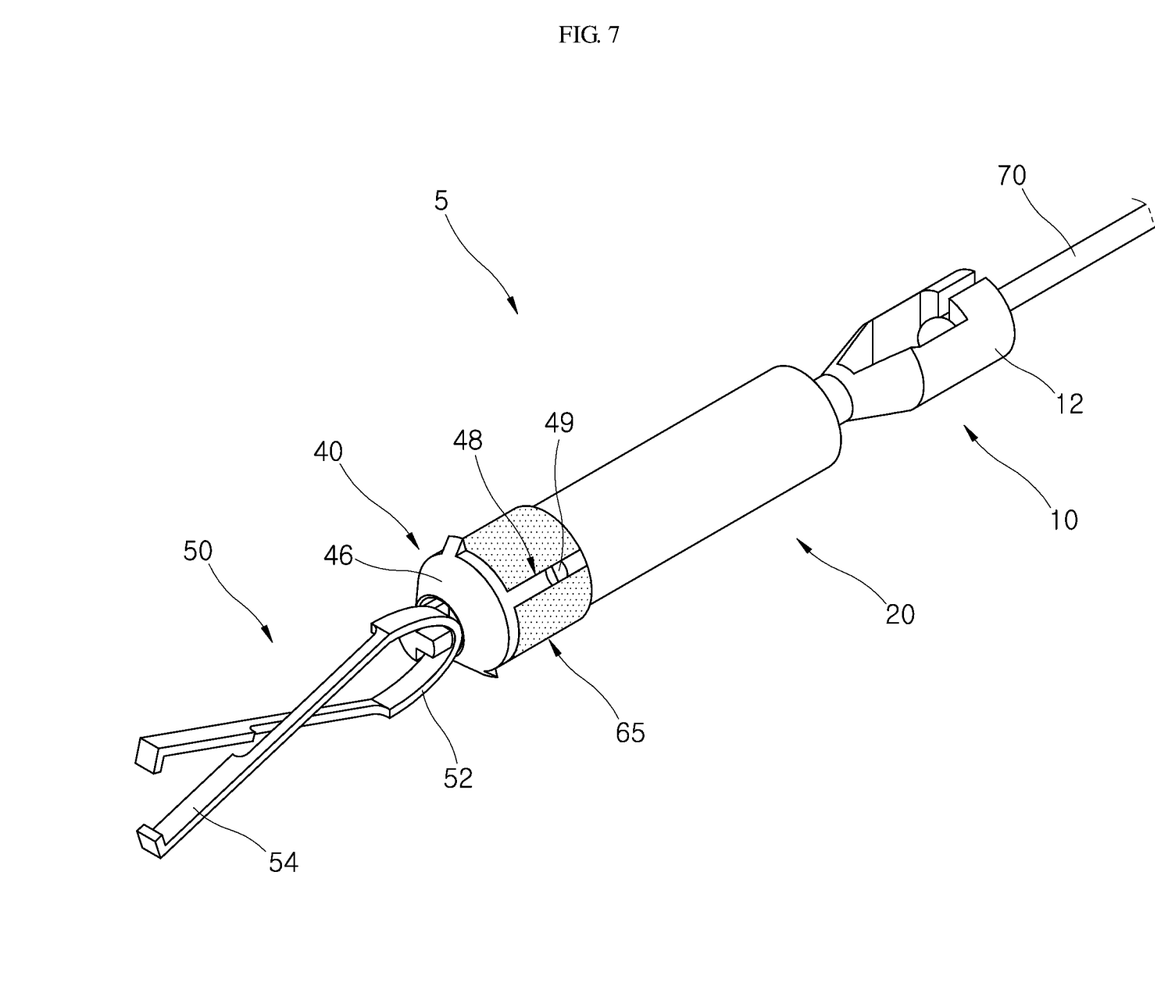
FIG. 7 is a perspective view of the clipping device for an endoscope according to another embodiment of the present invention.
Figure 8:
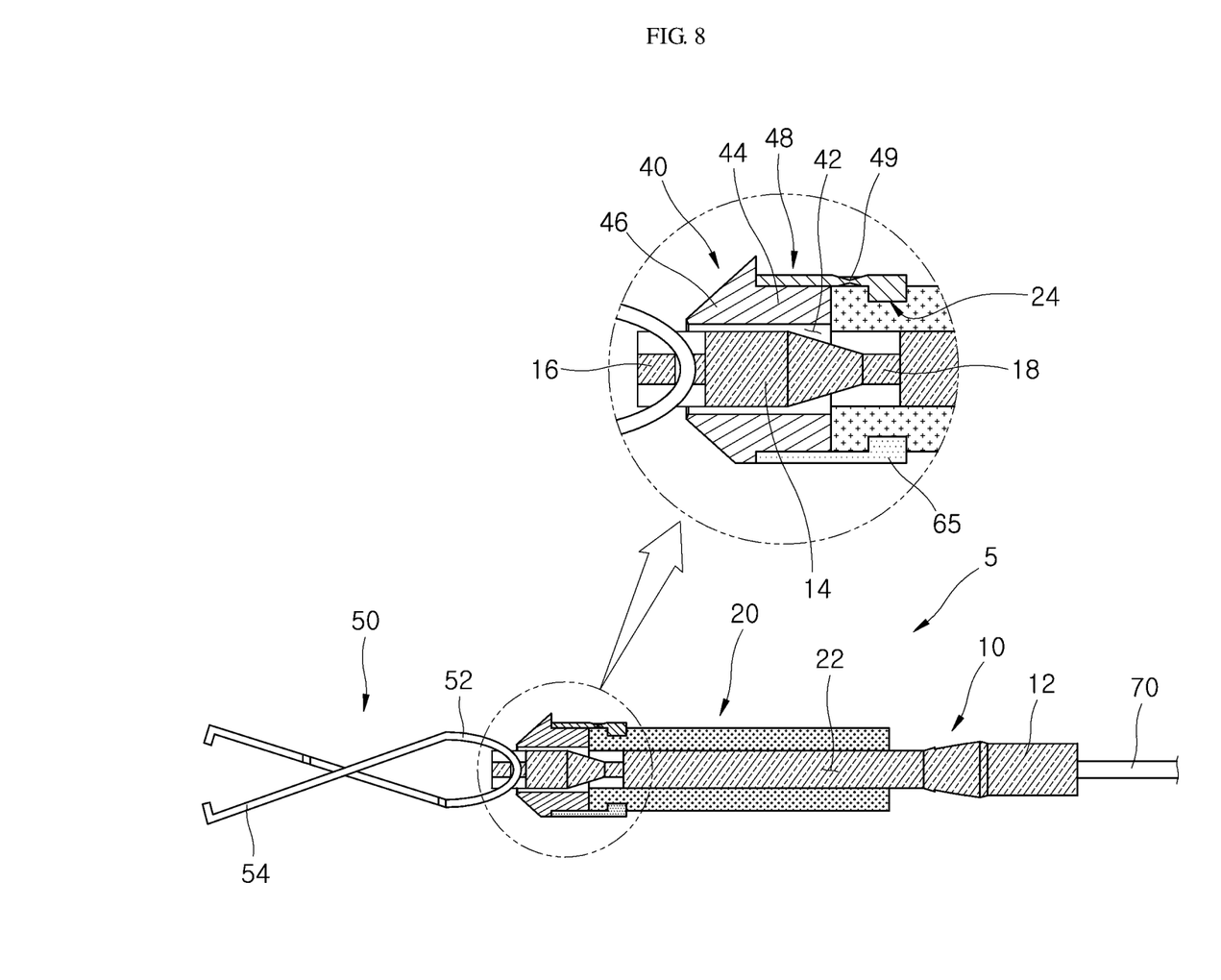
FIG. 8 is a cross-sectional view of the clipping device for an endoscope according to another embodiment of the present invention.
Figure 9:
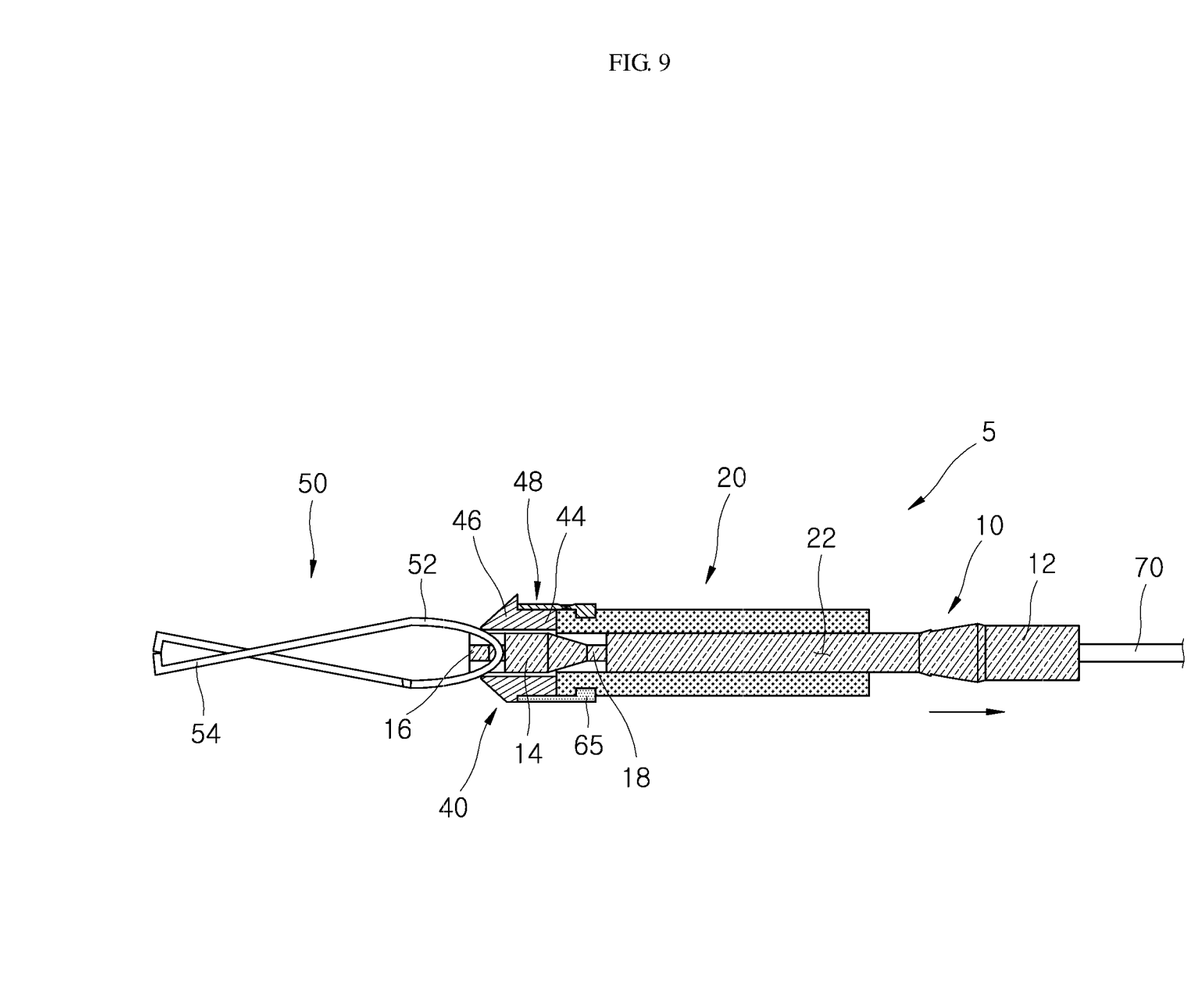
FIG. 9 is a cross-sectional view illustrating a state in which a clipping portion moves toward an inside of a cap portion along a connecting portion in the clipping device for an endoscope according to another embodiment of the present invention.
Figure 10:
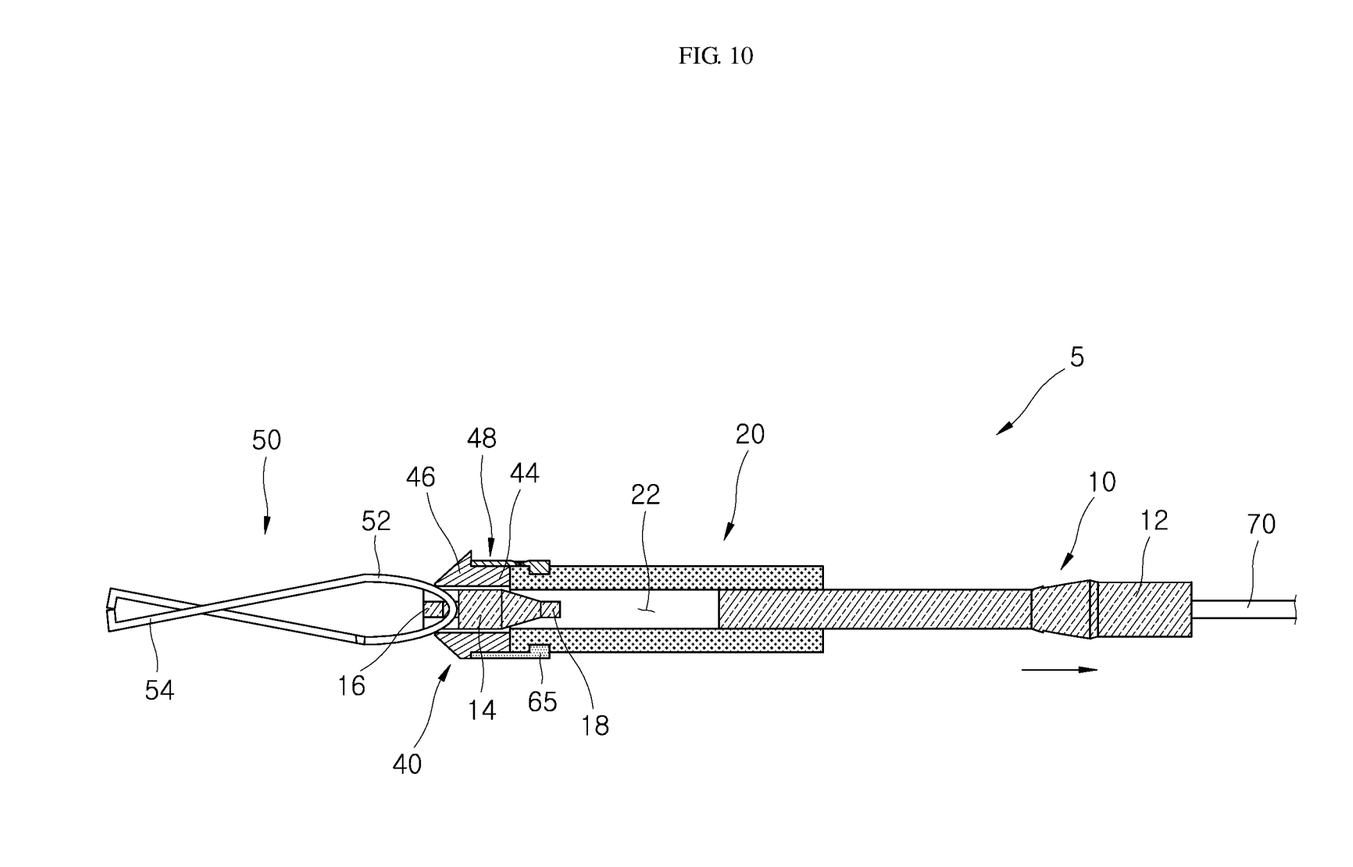
FIG. 10 is a cross-sectional view illustrating a state in which the connecting portion is broken according to another embodiment of the present invention.
Figure 11:
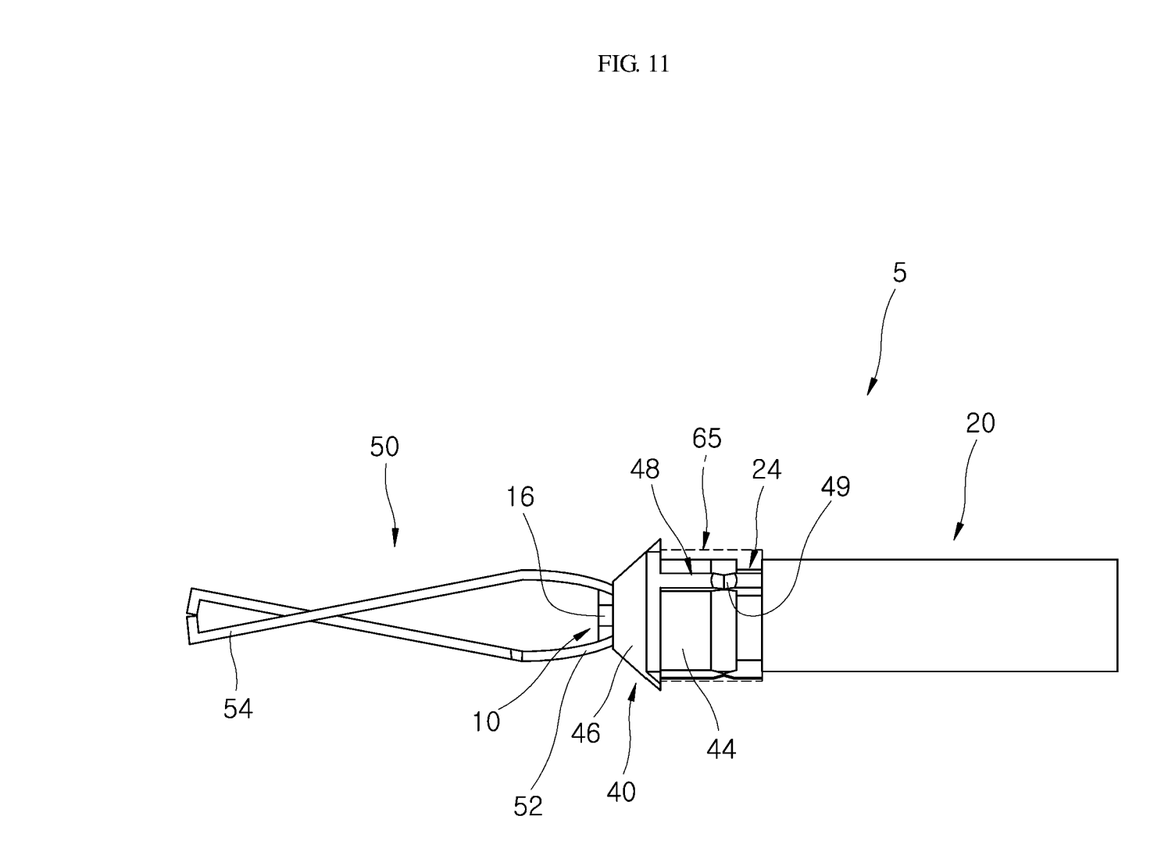
FIG. 11 is a view illustrating a state in which a first body is completely separated from the clipping device for an endoscope according to another embodiment of the present invention.
Figure 12:
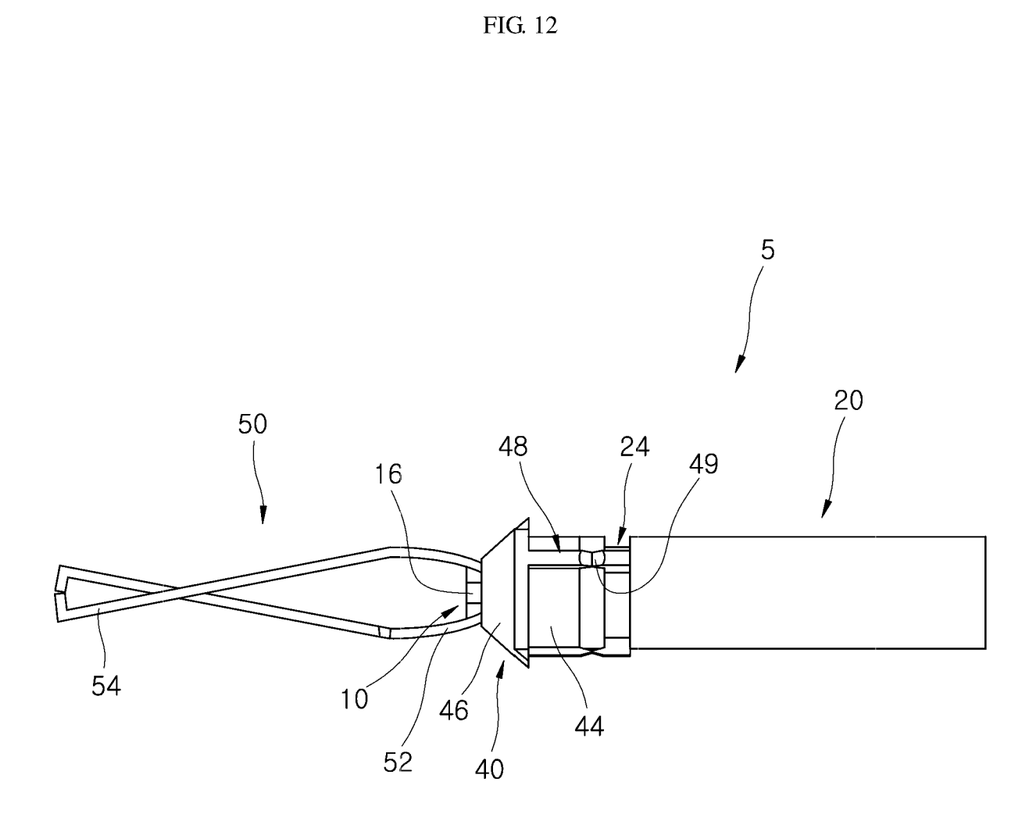
FIG. 12 is a view illustrating a state in which a connector has been biodegraded in the clipping device for an endoscope according to another embodiment of the present invention.
Figure 13:
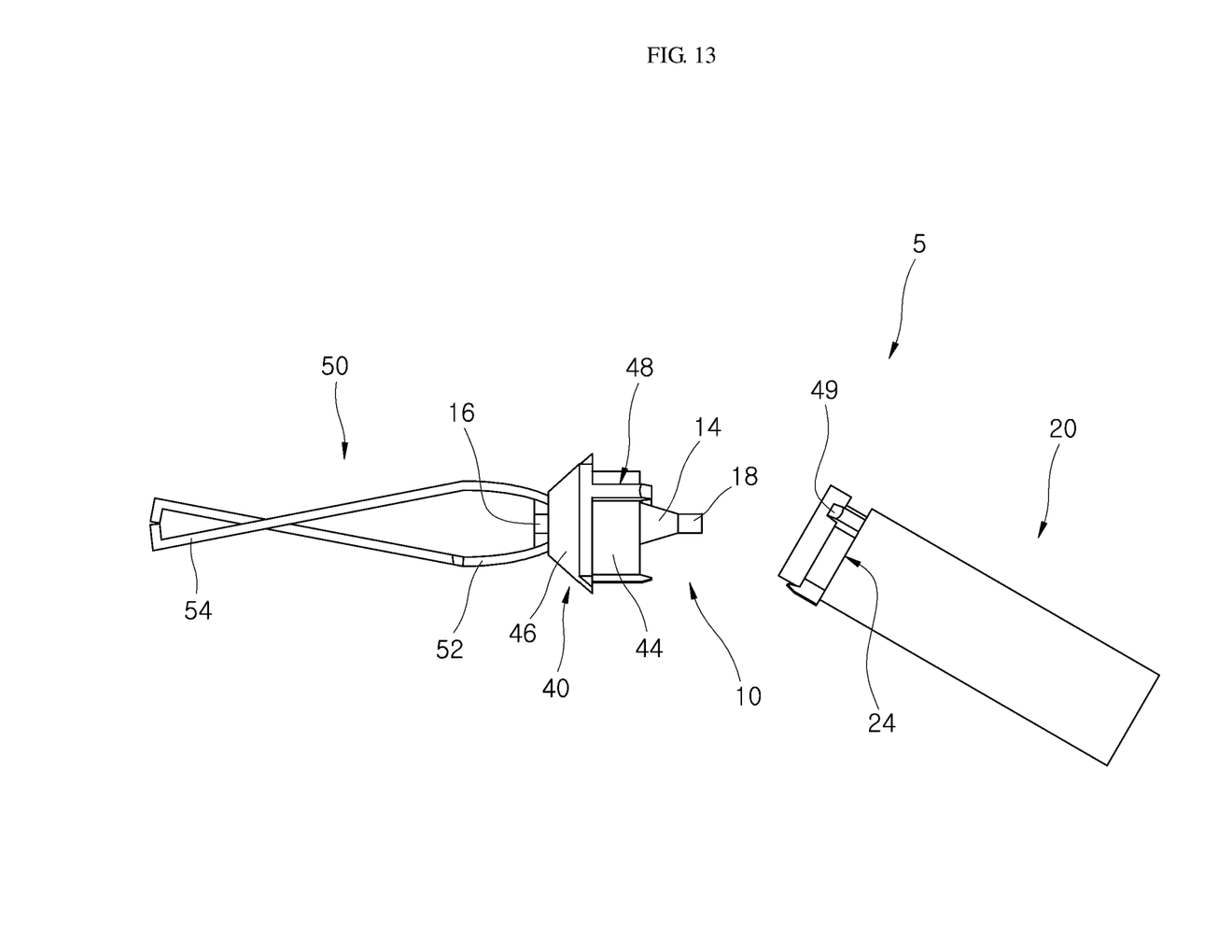
FIG. 13 is a view illustrating a state in which a cap portion has been separated from a body portion according to another embodiment of the present invention.

FIG. 6 is an exploded perspective view of a clipping device for an endoscope according to another embodiment of the present invention. FIG. 7 is a perspective view of the clipping device for an endoscope according to another embodiment of the present invention. FIG. 8 is a cross-sectional view of the clipping device for an endoscope according to another embodiment of the present invention. FIG. 9 is a cross-sectional view illustrating a state in which a clipping portion moves toward an inside of a cap portion along a connecting portion in the clipping device for an endoscope according to another embodiment of the present invention. FIG. 10 is a cross-sectional view illustrating a state in which the connecting portion is broken according to another embodiment of the present invention. FIG. 11 is a view illustrating a state in which a first body is completely separated from the clipping device for an endoscope according to another embodiment of the present invention. FIG. 12 is a view illustrating a state in which a connector has been biodegraded in the clipping device for an endoscope according to another embodiment of the present invention. FIG. 13 is a view illustrating a state in which a cap portion has been separated from a body portion according to another embodiment of the present invention.

The clipping device 5 for an endoscope according to another embodiment of the present invention includes a connecting portion 10, a body portion 20, a cap portion 40, a clipping portion 50, and a connector 65. Since the connecting portion 10, the body portion 20, and the clipping portion 50 are the same as those of one embodiment of the present invention, a description thereof will be omitted.

The cap portion 40 according to another embodiment of the present invention includes a first support body 44, a second support body 46, and a cap connecting portion 48.

The first support body 44 has a pipe shape in contact with an end of the body portion 20 and has an outer diameter smaller than an outer diameter of the body portion 20. The second support body 46 is connected to the first support body 44 with a step therebetween and has a conical shape toward a direction in which the clipping portion 50 is installed. The cap connecting portion 48 extends from the second support body 46, is held by a combination groove 24 provided outside the body portion 20, and includes a break connecting member 49 broken by a set external force. The cap connecting portion 48 extends in a shape of a strap around the second support body 46, and one end of the cap connecting portion 48 has a hook shape held by the combination groove 24. Since a groove portion having a notch shape is formed at the break connecting member 49, the break connecting member 49 is more easily broken by an external force than other parts of the cap connecting portion 48. A second inside path portion 42 is formed inside the first support body 44 and the second support body 46 and is connected to a first inside path portion 22 of the body portion 20.

The connector 65 formed of a material biodegradable in a human body is installed in a shape which surrounds an outside of the first support body 44 and an outside of the body portion 20 facing the first support body 44. One side of the connector 65 is installed in a shape which surrounds the outside of the first support body 44 of the cap portion 40, and the other side of the connector 65 forms a protrusion inserted into the combination groove 24 formed outside the body portion 20 and is installed in a shape which surrounds the outside the body portion 20.

Accordingly, the body portion 20 and the cap portion 40 of the clipping device 5 for an endoscope are primarily connected to the connector 65 and are secondarily connected to the cap connecting portion 48 of the cap portion 40. The connector 65 is naturally decomposed in a human body, and a connection by the cap connecting portion 48 is released by an operation of cutting the break connecting member 49.

Hereinafter, an operation state of the clipping device 5 according to another embodiment of the present invention will be described in detail with reference to the attached drawings.

As shown in FIGS. 6 to 8, the clipping device 5 is inserted into a human body while the clipping portion 50 is open. As shown in FIG. 9, the clipping portion 50 and the connecting portion 10 are moved together toward an inside of the cap portion 40 by an operation of moving the connecting portion 10 by pulling the wire 70, whereby both ends of the clipping portion 50 are collected and fixed to body tissue.

When the wire 70 is pulled again as shown in FIG. 10, a breaking body 18 of the connecting portion 10 is broken, and the first body 12 and the wire 70 come out from the human body together. As shown in FIGS. 11 and 12, when the connector formed of a material biodegradable in a human body is gradually melted and removed, the connection between the cap portion 40 and the body portion 20 is maintained by only the cap connecting portion 48.

Accordingly, as shown in FIG. 13, since the break connecting member 49 of the cap connecting portion 48 is cut using forceps, the body portion 20, which is magnetic, is separated from the cap portion 40. The separated body portion 20 is discharged outward from the human body by a suction device.

As described above, according to the embodiments of the present invention, since the body portion 20, which is magnetic, is easily separated from the clipping portion 50 as the connector 65 biodegradable in the human body is melted, the body portion 20 may be quickly removed.

According to the embodiments of the present invention, in a clipping device for an endoscope, as a connector, which is biodegradable in a human body, is melted, a body portion having a magnetic force is easily separated from a clipping portion so as to quickly remove the body portion.

Although the present invention has been described with reference to the embodiments shown in the drawings, it should be understood that the embodiments are merely examples and a variety of modifications and equivalents thereof may be made by one of ordinary skill in the art. Accordingly, the veritable technical scope of the present invention will be defined by the following claims.

What is claimed is:

1. A clipping device for an endoscope, comprising:
    a connecting portion having a breaking body, the connecting portion configured to be moved while being connected to a wire of the endoscope;

a body portion including a first inside path portion through which the connecting portion moves and which has a magnetic force;

a cap portion located on a side of the body portion, the cap portion including a second inside path portion connected to the first inside path portion, and configured to guide movement of the connecting portion;

a clipping portion connected to the connecting portion and configured to contract due to movement of the connecting portion to grip body tissue; and a connector connecting the body portion to the cap portion and including a material biodegradable in a human body, wherein the cap portion comprises:

a first cap body in contact with an end of the body portion;

a second cap body spaced apart from the first cap body; and a connecting body connecting the first cap body to the second cap body and including an outer diameter smaller than an outer diameter of the first cap body, and wherein the second inside path portion is formed inside the first cap body, the connecting body, and the second cap body.

2. The clipping device of claim 1, wherein the connecting portion comprises:

a first body configured to be connected to the wire;

a second body connected to the clipping portion; and the breaking body connecting the first body to the second body and configured to break, disconnecting the first body and the second body when the breaking body is broken.

3. The clipping device of claim 1, wherein the body portion has a pipe shape, and both longitudinal sides of the body portion have magnetic forces of different polarities.

4. The clipping device of claim 3, wherein the body portion comprises a combination groove formed on an outside thereof to be combined with at least one of the cap portion and the connector.

5. The clipping device of claim 1, wherein the connector surrounds an outside of the connecting body and an outside of the body portion facing the connector.

6. The clipping device of claim 1, wherein the connector comprises gelatin.

\* \* \* \* \*